(12) United States Patent
Harris et al.

(10) Patent No.: US 9,566,560 B2
(45) Date of Patent: Feb. 14, 2017

(54) ARRAY DOMAINS HAVING ROTATED PATTERNS

(75) Inventors: Jason Harris, San Ramon, CA (US); Stephen Tanner, San Diego, CA (US)

(73) Assignee: Illumina, Inc., San Diego, CA (US)

( * ) Notice: Subject to any disclaimer, the term of this patent is extended or adjusted under 35 U.S.C. 154(b) by 808 days.

(21) Appl. No.: 13/267,565

(22) Filed: Oct. 6, 2011

(65) Prior Publication Data

US 2013/0091176 A1    Apr. 11, 2013

(51) Int. Cl.
*C12Q 1/68* (2006.01)
*B01J 19/00* (2006.01)

(52) U.S. Cl.
CPC ... *B01J 19/0046* (2013.01); *B01J 2219/00527* (2013.01); *B01J 2219/00605* (2013.01); *B01J 2219/00608* (2013.01); *B01J 2219/00659* (2013.01); *B01J 2219/00662* (2013.01); *B01J 2219/00693* (2013.01); *B01J 2219/00722* (2013.01); *C12Q 1/6837* (2013.01)

(58) Field of Classification Search
None
See application file for complete search history.

(56) References Cited

U.S. PATENT DOCUMENTS

| | | | |
|---|---|---|---|
| 4,583,298 A | 4/1986 | Rough | |
| 4,745,633 A | 5/1988 | Waksman et al. | |
| 5,798,947 A | 8/1998 | Ye et al. | |
| 6,498,010 B1 * | 12/2002 | Fitzgerald et al. | 435/6.11 |
| 6,548,768 B1 | 4/2003 | Pettersson et al. | |
| 6,570,104 B1 | 5/2003 | Ericson et al. | |
| 6,663,008 B1 | 12/2003 | Pettersson et al. | |
| 6,667,695 B2 | 12/2003 | Pettersson et al. | |
| 6,676,602 B1 | 1/2004 | Barnes et al. | |
| 6,948,254 B2 | 9/2005 | Stiblert et al. | |
| 7,145,556 B2 | 12/2006 | Pettersson | |
| 7,231,063 B2 | 6/2007 | Naimark et al. | |
| 7,249,716 B2 | 7/2007 | Bryborn | |
| 7,600,693 B2 | 10/2009 | Pettersson | |
| 2002/0064774 A1 | 5/2002 | Schembri | |
| 2003/0045005 A1 | 3/2003 | Seul | |
| 2004/0126766 A1 * | 7/2004 | Amorese | 435/6 |
| 2005/0112587 A1 | 5/2005 | Sherrill | |
| 2008/0117425 A1 | 5/2008 | Kain | |
| 2010/0041566 A1 * | 2/2010 | Zhang et al. | 506/9 |

FOREIGN PATENT DOCUMENTS

EP    1481727 A2    12/2004

OTHER PUBLICATIONS

Sauer et al., Nature Genetics, 2005, vol. 6, pp. 465-476.*
Chang, Journal of Immunological Methods, 1983, vol. 65, pp. 217-223.*
Efrat, et al., "Subpixel Image Registration Using Circular Fiducials", International Journal of Computational Geometry & Applications, 1994, 1-20.
O'Gorman, et al., "A Comparison of Fiducial Shapes for Machine Vision Registration", IAPR Workshop on Machine Vision Applications, 1990, 253-256.
Wyawahare, et al., "Image Registration Techniques: An overview", International Journal of Signal Processing, Image Processing and Pattern Recognition, vol. 2, No. 3, 2009, 11-28.
International Search Report and Written Opinion mailed Dec. 17, 2012 for PCT/US2012057512.

* cited by examiner

*Primary Examiner* — Mindy G Brown
(74) *Attorney, Agent, or Firm* — Fletcher Yoder, P.C.

(57) ABSTRACT

An article of manufacture having a plurality of sites in domains of regular patterns. Neighboring domains are oriented at different angles to improve the identification of the sites.

25 Claims, 6 Drawing Sheets

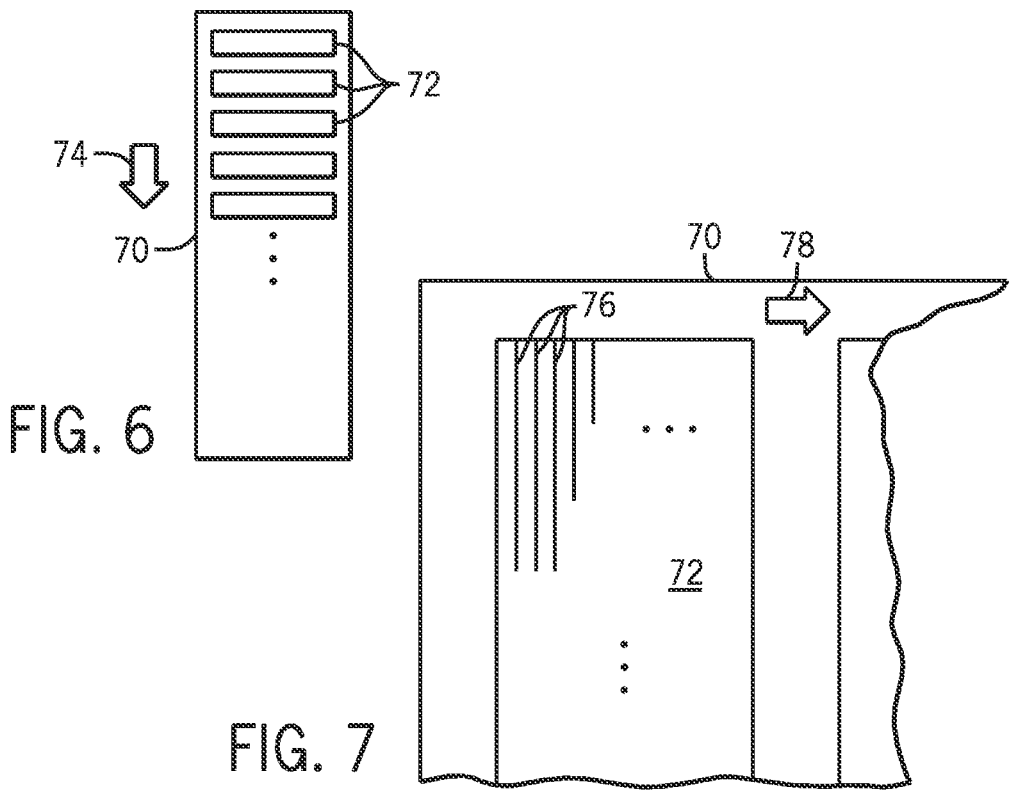
FIG. 6
FIG. 7
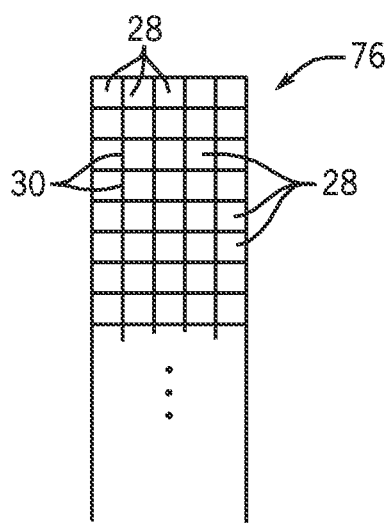
FIG. 8 ered arrays.

ARRAY DOMAINS HAVING ROTATED PATTERNS

BACKGROUND

The invention relates generally to the field of patterned arrays. More particularly, the invention relates to novel arrangements of layouts that improve the location and identification of specific sites on the arrays.

Arrays provide a number of individual sites at permanently or transiently fixed locations on a surface. Particularly useful arrays have sites that contain chemical groups or biological molecules, which can be identical or different among the many sites, and can interact with other materials of interest, such as a biological sample. Sites can be located by taking an image of the substrate surface, such as by a planar image or by line scanning. The image data is processed to locate and identify at least a portion of the sites. Where a chemical or biological interaction occurs at a particular site, the interaction can also be detected at the site and correlated with the location and identity of the site, as well as the particular group or molecule present at the site.

Sites are frequently arranged in a regular geometrical pattern, such as a checkerboard or hexagonal grid, to maximize the number of sites available on the substrate surface and to facilitate the location of sites by automated instruments. The location of individual sites on a surface can be identified by various registration methods. Conventional registration (sometimes referred to as "full registration") is based on starting from predetermined locations within the array and advancing through the sites one at a time by expected location. An example of a full registration algorithm uses one or more reliable reference location ("fiducial") such as an edge or other identifiable landmark. The sites in a regular pattern can then be identified using the fiducials for absolute reference, proceeding through the rows (or columns) based on knowledge a priori of the geometrical pattern, site size and pitch (spacing), collectively a "reference pattern". Full registration for every site on a substrate can be mechanically and computationally burdensome, however, due to the difficulty of accurately measuring absolute distances from a few reference points that are relatively distant.

To supplement full registration methods, local registration can be performed rapidly using a simple two-dimensional cross-correlation between the signals in detected site locations and the reference pattern. The alternate approach might be termed "rigid registration". While the method can be based in part on the ability to detect fiducials, the rigid approach takes advantage of knowledge a priori of the pattern (such as hexagonal), so that the location an individual site can be fine-tuned locally by observing its position relative to its neighbors. For example, a least squares fit can be performed with the detected signal against a rigid grid of coordinates (such as a kernel hexagonal array) serving as the reference pattern. The fit is completed via an affine transformation to account for large scale distortions that can be present throughout the image. In some registration methods, the local registration is sufficiently robust to obviate the necessity for measuring each location absolutely with respect to the fiducials, so that full registration is performed only at predetermined intervals, reducing the overall burden of the registration method. The locations can be registered simultaneously rather than one at a time, with a reduced sensitivity to large-scale distortions.

Nevertheless, the fitting routine is computationally expensive for large area arrays with a large number (high density) of objects. An additional challenge with the approach is that it is not sensitive to local, small scale distortions; such distortions can similarly induce miscorrelation between the detected array and the kernel. Thus, the rigid registration algorithm may not be ideally suited to large area microarrays.

Unfortunately, cross-correlation checks are not always sensitive to integral offsets (such as vertical or horizontal translation) or "walk-offs", where the registration can appear correct locally within a geometrical pattern of sites, but each site is mistaken for its neighbor. Reliance on local registration can also break down if attempted from within the repeating expanse of a regular pattern, without the absolute reference of a fiducial. Although some walk-off errors can be corrected when a fiducial is subsequently found, walk-offs can accumulate so that the compounded error can be difficult to resolve unambiguously. Where the correct identification of a site is significant, such as with random bead arrays, the correlation of an interaction with the wrong site location can result in an erroneous interpretation. Thus, there is a need for an arrangement of sites that is resistant to walk-off errors.

SUMMARY

The present invention provides an article of manufacture, comprising a substrate (70), on which a plurality of sites (12) are disposed at fixed, physical locations on the surface of the substrate. An example of such an article is an ordered array or microarray, where optionally some or all of the sites may be configured to hold a material of interest.

The sites are organized primarily in a plurality of domains (28), where each domain has a layout of sites. In some configurations, if two domains share a common edge, then they do not have the same layout (although they may share the same regular pattern in one rotation or another).

In a (first) domain, for example, the sites can be arranged in a first layout (32) to form a regular pattern. A regular pattern is translationally periodic, repeating in one or more directions. Some regular patterns have one or more rotational symmetries and can be described as oriented at a (first) angle (36). Examples of periodic patterns include a checkerboard grid or a hexagonal grid. A neighboring (second) domain has a second layout (34) where the sites are arranged in the regular pattern oriented at a (second) angle (40) that is different from the first angle.

Sets of two or more domains can be organized in one or more sample areas (72), where each sample area has two or more two nonoverlapping domains (28) adjacent to each other. In some configurations, the areas that border (30) neighboring domains can contain sites or not contain sites, depending on the integrity of maintaining the pattern of the domain. Separate sample areas can be useful if identical sets of the same domains are provided for each sample area, such as to present multiple samples with the same set of domains for an apples-to-apples comparison.

In FIG. 2, for example, a regular hexagonal pattern of a domain (32) exhibits an orientation (36) and at least one angle interval of rotational symmetry (∠ 36 38), namely 60 degrees. Of course, hexagonal patterns (10) have multiple equivalent angles of orientation (20, 22, 24, etc.). The angle of a neighboring domain (34) can be oriented at 30 degrees (40), which is different from the 60-degree angle interval. Even though two adjacent domains (32, 34) have the same regular pattern (hexagonal), the sites in the two domains are distinguishable by their different orientations (36 versus 40).

As another example, the sample area (48) in FIG. 4 has four domains (52, 56, 52, 50) arranged in two rows (44) and two columns (46). Each of the four domains has a regular hexagonal pattern of sites (10) that can be described as "polyhexagonal". Relative to the first domain (52), which is nominally oriented at 0 degrees (∠ 58 64), the hexagonal patterns of the second (56), third (52) and fourth (50) domains are oriented about 15 degrees (∠ 58 66), 30 degrees (∠ 58 62), and 45 degrees (∠ 58 60), respectively. None of these orientations are equal to the 60-degree angle interval that is characteristic of the hexagonal pattern, or equal to each other.

While the sites refer to fixed, discrete physical locations on the surface of the substrate, in some embodiments the sites can contain chemical moieties (such as reactive chemical groups), binding ligands, or biological molecules, such as oligonucleotides or polypeptides. The sites themselves can be the flat surface of the substrate, or can take the form of wells, which can contain beads for attachment to the chemical moieties.

The invention also offers methods for making such articles. In one implementation, the method comprises forming a plurality of sites on a substrate as described above.

In a particular embodiment, the invention provides methods for processing information. For example, one such method may comprise disposing material on interest at sites on an article, such as an array or microarray.

The present invention also provides a method of (a) providing the article of the invention; (b) locating the sites; and (c) identifying individual sites by their location. The identifying step can comprise correlation of the pattern of the domain against a reference pattern for the domain. The steps may be repeated, such as for sequencing or for any other analytical purpose.

BRIEF DESCRIPTION OF THE DRAWINGS

These and other features, aspects, and advantages of the present invention will become better understood when the following detailed description is read with reference to the accompanying drawings, in which like characters represent like parts throughout the drawings, wherein:

FIG. 6 is a plan view of an exemplary substrate (70) with several sample areas (72);

FIG. 7 is a more detailed view of an exemplary sample area (72) of the substrate of FIG. 6, illustrating a number of parallel scan lines that can be used to image and identify of the location and characteristics of sites within one or more regions of a section (76);

FIG. 8 is a still more detailed view of exemplary domains (28) within a section (76) of the sample area shown in FIG. 7;

DETAILED DESCRIPTION

Figure 1:
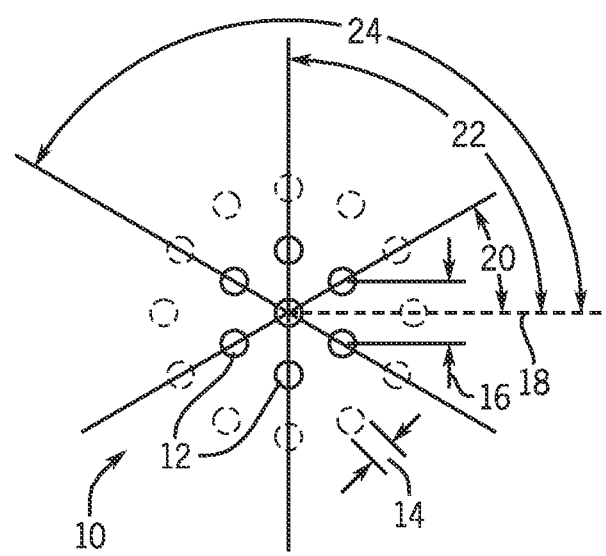
FIG. 1 is a plan view of an exemplary layout of sites (12) in an exemplary hexagonal pattern (10)

The present invention provides for dividing a sample area into a series of domains, and rotating the layout of adjacent domains by predetermined angles so that no two domains that share an edge will have the same rotation orientation relative to the coordinate system defined by the active area of the array.

In certain embodiments, the number of domain layout rotations is limited so that any particular domain layout will not be rotated into the orientation of any neighboring domain(s) or its own pre-rotated hexagonal configuration (e.g., 60 degrees or integral multiples thereof). Similarly, the number of objects of each domain can either be constant or variable over all domains comprising the array.

The combination of layouts with rigid registration, however, provides a framework for alternative processing in the form of a locally rigid registration algorithm for robust and efficient registration of domains of the substrate. By dividing the array into domains (with layouts rotated as mentioned above), each domain can be registered accurately and efficiently using the rigid registration algorithm and, subsequently, the set of registered domains can be pieced together to form a final registered substrate read.

Added advantages of the approaches include, due to the reduced size of the domains relative to the complete array, the rigid registration algorithm becomes sensitive to local distortions in the detected signals. Moreover, the efficiency of performing a least-squares fit is increased as the number of objects in each domain is decreased, and thus the efficiency of rigid registration over full registration is realized. Furthermore, the multitude of domains enhances the sensitivity of the two-dimensional cross-correlation check of the registered objects with the kernel array. With the domain array format, the two-dimensional cross correlation is now extremely sensitive to distortions, such as walk-off of the registered objects by integral values of the pitch, because the correlation signal will greatly decrease for domains that are rotated relatively to the domain that induced the walk-off. The sensitivity of the cross correlation check will be a function of the number of different domains included in the array design. For example, if two domain angles are used in the design, then one half of the cross-correlation signal can be lost if a walk-off is experienced, and therefore this check can suggest that a registration failure has taken place.

In certain embodiments, it may be advantageous to include an isolated object in the overall pattern to aid in the construction of an empirical profile for each individual object. For example, if the detection technique is to optically image the substrate, an empirical sampling of the optical point spread function can facilitate an accurate extraction of each object's real signal when in the proximity of other object's signals (object-to-object cross talk). The isolated object must be identical in nature to those objects comprising the substrate with the fundamental difference being that the object used for empirical sampling of the object signal is not surrounded by neighbor objects. The reason for the isolation is to eliminate the signal-to-signal cross talk. The empirical profile facilitates an exact deconvolution of the signal observed at a particular location within the substrate from the signal arising at that same location from all other objects.

FIG. 1 shows an exemplary layout for sites within domains of a substrate. The hexagonal pattern, designated generally by the reference numeral 10, comprises a plurality of individual sites 12 at which biological material of interest may be deposited. The sites may have different dimensions and may be regular or somewhat irregular. However, in a presently contemplated embodiment, the sites are generally circular, with a diameter 14 that is generally uniform. The sites are spaced from one another by a minimum distance or pitch 16, which is also uniform. The layout of the sites is generally hexagonal, with a site at the center of each hexagon defined by neighboring sites, as shown. While a wide range of dimensions and pitches may be employed, presently contemplated dimensions of the sites are based on beads disposed at the sites, the beads having a nominal diameter of 1.2 microns. The pitch selected will provide a distance between the sites to allow for close packing (high density), while sufficiently avoiding crosstalk that may adversely affect data analysis. For example, currently contemplated pitches include 1.70 microns, 1.85 microns and 2.0 microns. For smaller sites, on the order of 100-500 nanometers in diameter, smaller pitches, such as on the order of 1.2 microns or smaller may be used. In presently contemplated embodiments, for example, the pitch may be approximately 30% above the diameter of the sites (or beads). It should be borne in mind, however, that these dimensions and pitches are exemplary only. Similarly, while presently contemplated embodiments employ bead technologies, other site-forming technologies may also be used.

The hexagonal pattern 10 of the sites 12 naturally provides linear alignments of the sites that are angularly-displaced from one another by 60 (or 120) degrees. That is, for the layout illustrated in FIG. 1, a nominal or reference direction 18 may be designated, in this case extending generally horizontally. The hexagonal pattern, then, provides sites aligned along a line at a first angle 20, along a line at a second angle 22, and along a line at a second angle 24. Because each of these lines is progressively 60 degrees rotated from the preceding line, in the illustrated example, the angle 20 is 30 degrees with respect to reference direction 18, while angles 22 and 24 are 90 and 150 degrees, respectively.

A hexagonal pattern of the sites may be rotated into different layouts for the various domains of the substrate. That is, each domain will maintain the high density packing of sites offered by the hexagonal pattern, but the lines along which the sites are naturally aligned will be oriented differently in different domains. As discussed below, it has been found that the potential for error in assignment of addresses based on image data collected from the resulting substrates is significantly reduced, and processing and analyzing the data are significantly improved.

Figure 2:
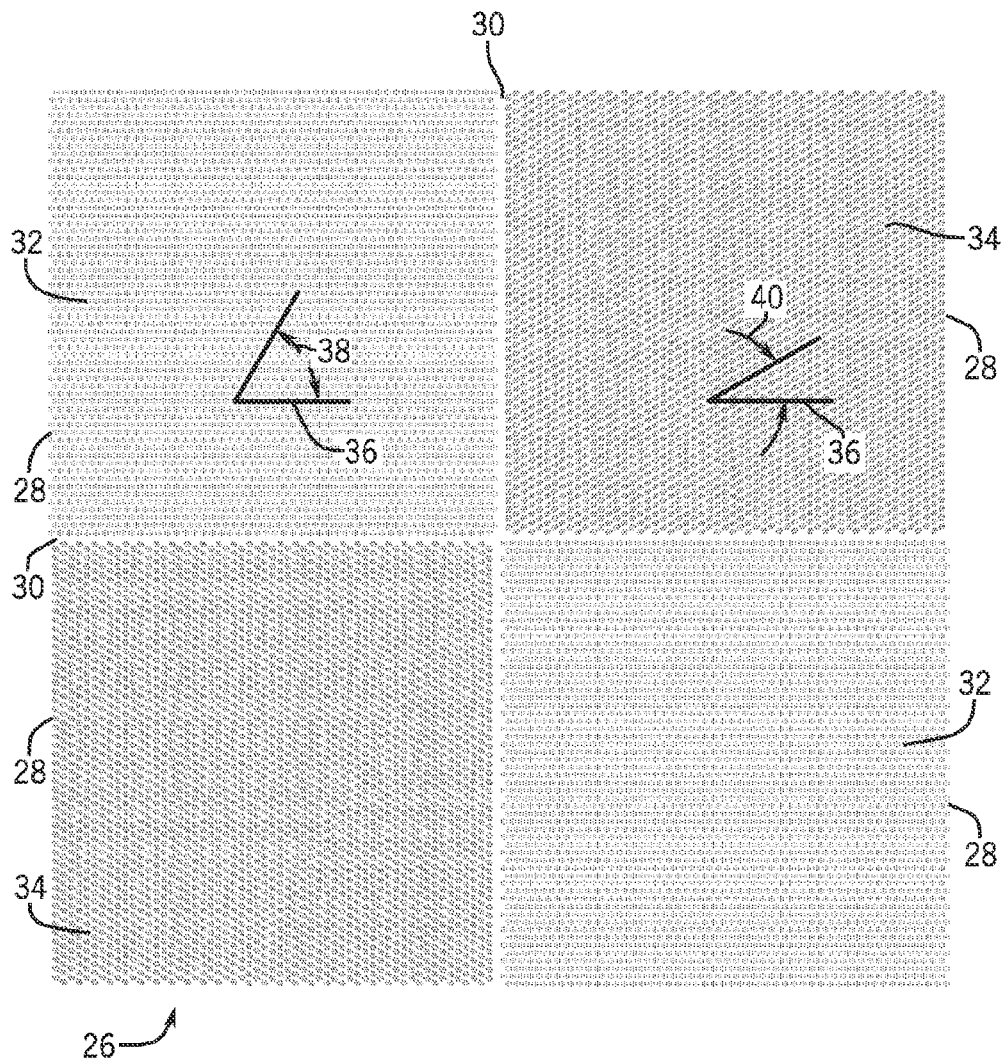
FIG. 2 is a plan view of an exemplary embodiment of a sample area (26) having four domains, with two different angularly-displaced hexagonal patterns (32, 34) of sites.

FIG. 2 illustrates a first exemplary embodiment in which two different hexagonal pattern orientations are employed. This embodiment may be considered to be based upon a "couplet" of domains, each with a hexagonal pattern of sites at a unique orientation. The sample area 26 thus comprises domains 28 separated by edges 30, with the domains themselves comprising a first layout, as indicated by reference numeral 32, and a second layout, 34. As summarized above with reference to FIG. 1, the layouts may be considered with regard to a reference direction, labeled 36 in FIG. 2. In this embodiment, the first layout 32 has sites aligned a first line at an angle 38 of 60 degrees (or 0 degrees) with respect to the reference direction, and then along lines at 60 degree intervals thereafter. The second layout 34, on the other hand, has sites aligned along a first line at an angle 40 of 30 degrees with respect to the reference direction (i.e., in the reference direction) and then similarly along lines at 60 degree intervals thereafter. That is, the layouts may be said to be angularly oriented or displaced 30 degrees with respect to one another.

In one presently contemplated embodiment, the domains have approximately the same number of sites, although precise number may vary due to the allowance for edges between the domains. In a presently contemplated embodiment, the domains comprise at least 10×10, 25×25, 50×50, 100×100 sites. Other numbers of sites may, of course, be used, and the domains need not be square or of any particular shape. Moreover, it should be borne in mind that the particular angles of rotation of the layouts 32 and 34 with respect to one another, or with respect to a particular reference direction may differ from that illustrated in this example. In general, the angle of rotation will be sufficiently large to be observable by equipment used to read the substrate, and sufficiently small to avoid similarity between the domains. Presently contemplated differences in orientation between the domains include 10, 15, 20, 25, and 30 degrees, although, again, any desired angles may be used, particularly depending upon the number of different domains (e.g., 2 as in the example of FIG. 2, 4 as discussed below, or more).

Figure 3:
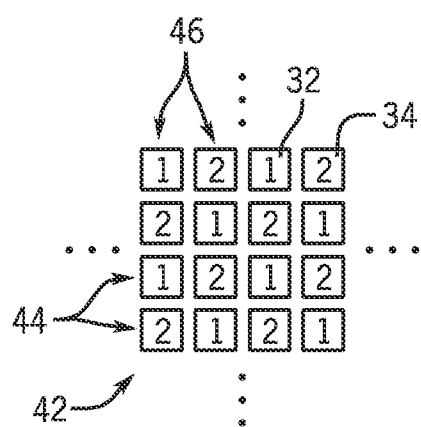
FIG. 3 shows an exemplary manner in which the domains of FIG. 3 might be organized in a section of a substrate.

FIG. 3 illustrates an exemplary organization 42 of the domains of FIG. 2. In this organization, the domains are positioned such that no neighboring domains (i.e., domains sharing a common edge) have the same layout. The domains are laid out in a rectilinear grid (although other grids could be used) having rows 44 and columns 46. The rows and columns thus have the two domain layouts comprising the couplet in alternating orders forming a checkerboard-like organization. Using this organization, any number of domains may comprise a region or section of the substrate. In a present contemplated embodiment, for example, each section has from 5 to 10 domains in one direction by 100 domains in the opposite direction. Other sizes and numbers of domains may, of course, be used.

Figure 4:
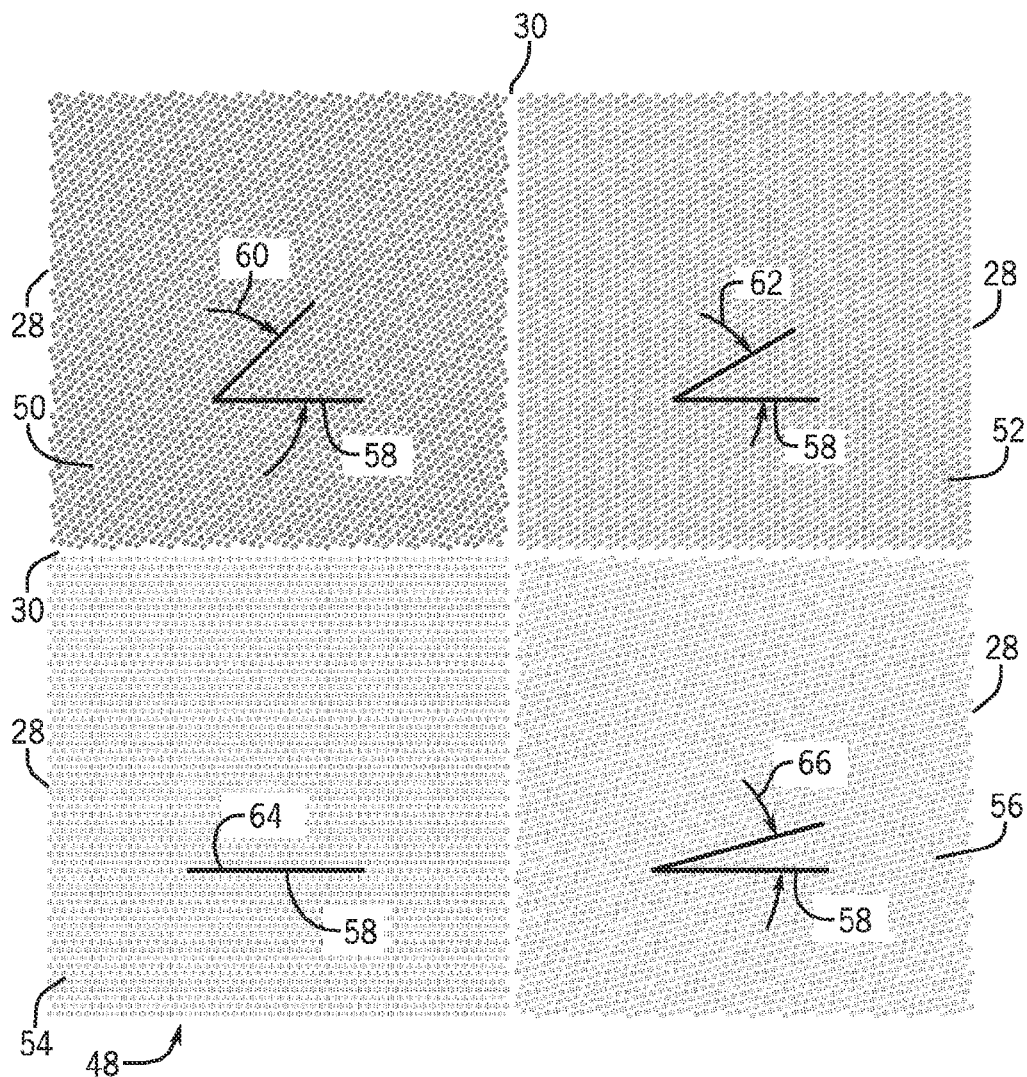
FIG. 4 is a plan view of another exemplary embodiment of four domains (54, 56, 52, 58), where each domain has a different angularly-displaced layout of hexagonally-disposed sites.

As noted above, a range of different layouts and orientations of the basic hexagonal pattern may be used, each defining a unique layout for the domains in the polyhexagonal sample areas. FIG. 4 illustrates an embodiment having 4 different domains, which may be termed a "quartet". This layout, designated generally by reference numeral 48, thus has first, second, third and forth domains 50, 52, 54 and 56, each having hexagonal patterns rotated with respect to one another. As before, a reference direction 58 may be considered for comparison purposes. In the illustrated embodiment, domains 50, 52, 54 and 56 each have a first line along with sites are aligned, oriented at unique angles 60, 62, 64 and 66, respectively, with similar lines of site alignment found at 60 degree increments thereafter in all domains. For the illustrated domains, these initial angles are 45, 30, 0 and 15 degrees, respectively. The domains may thus be considered to be rotated by 15 degrees with respect to one another. Here again, any desired angles could be used to define the 4 different domains of the quartet.

Figure 5:
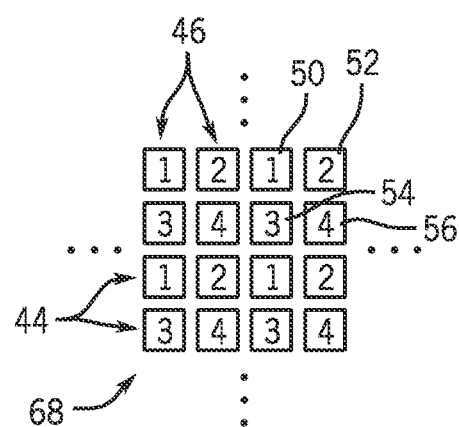
FIG. 5 shows an exemplary manner in which the domains of FIG. 4 might be organized in a section of a substrate.

As in the case of the couplet, it is believed that optimal performance may be obtained by positioning the domains of the quartet such that no similar domains share a common edge. One exemplary organization 68 is shown in FIG. 5. As with the couplets, the domains are organized in a rectilinear grid of rows 44 and columns 46, although other organizations could be used. Each row and column has alternating domain orientations of domains 50, 52, 54 and 56. As the number of different domains increases, the number of unique patterns available that satisfy the "different neighbor" criterion increases, and that shown in FIG. 5 is merely one example.

As noted above, it has been found that the use of different layouts for different domains reduces registration error due to shifts in registration, making appropriate indexing of the sites more certain. For example, a shift of sites by one pitch distance would result in 100% of the sites being wrongly indexed (as all sites, with the exception of edge sites, will overlie another site exactly. As the number of different layouts for the domains increases, the potential for such error is significantly reduced. In the case of quartets, as described with reference to FIGS. 4 and 5, the number of sites that could possibly overly one another is reduced to 25%.

It should also be noted that, while arrays of two and four different angularly different patterns have been described, practical implementations may include any desired number. For example, another presently contemplated embodiment includes 9 different patterns arranged in neighborhoods of domains in which no two similarly patterned domains share a boundary (i.e., they are not side-adjacent). Moreover, while hexagonal, or more generally, rotationally symmetrical patterns are presently contemplated, the patterns may adopt different layouts, and the differently patterned domains themselves may have different internal layouts (e.g., hexagonal, rectilinear, etc.). Still further, while the pitch and general size (e.g., number of sites) of the various domains are presently contemplated to be similar or nearly identical, this need not be the case (i.e., some domains may be differently sized, and even of substantially different sizes).

FIG. 6 illustrates an exemplary article of manufacture 70 in the form of a substrate that may make use of the polyhexagonal site layouts of the type described above. As shown in FIG. 6, a plurality of sample areas 72 may be provided that each will include a multitude of individual sites to be imaged organized in polyhexagonal patterns as described above. A wide range of layouts for such domains are possible, and the invention is not intended to be limited to any particular layout. As imaging progresses, as described below, the substrate 70 will be moved in an indexed direction 74 so that each of the sample areas 72 can be imaged.

An array laid out in the manners described herein can have a plurality of features including, for example, at least about 100, 500, 1000, 5000, $10^4$, $10^5$, $10^6$ or more features, with each of the features comprising a site which may contain biological material of interest that may be imaged and analyzed based upon the acquired image data. In particular embodiments, a bead-based array can be used in which microspheres or beads are arrayed or otherwise spatially distinguished. Exemplary bead-based arrays that can be used in the invention include, without limitation, those in which beads are associated with a solid support such as those described in U.S. Pat. No. 6,355,43; U.S. publication 2002/0102578; and international publication WO 00/63437, each of which is incorporated herein by reference. Beads can be located at discrete locations, such as wells, on a solid-phase support, whereby each location accommodates a single bead. Alternatively, discrete locations where beads reside can each include a plurality of beads as described, for example, in U.S. applications 2004/0263923, 2004/0233485, 2004/0132205, or 2004/0125424, each of which is incorporated herein by reference.

Any of a variety of arrays known in the art can be used in the present invention. For example, arrays that are useful in the invention can be non-bead-based. A particularly useful array is an Affymetrix GeneChip® array examples of which are described, for example, in U.S. Pat. No. 7,087,732 or 6,747,143, each of which is incorporated herein by reference. A spotted array can also be used in a method of the invention. An exemplary spotted array is a CodeLink™ array previously available from Amersham Biosciences. Another array that is useful in the invention is one manufactured using inkjet printing methods such as SurePrint™ technology available from Agilent Technologies. Arrays used in various sequencing platforms are also useful such as those used for Solexa sequencing technology as described, for example, in U.S. Publications 2007/0015200; 2004/0106110; 20030064398 or 2003/0022207; those used in 454 sequencing technology such as those described in U.S. Publication 2006/0040297 or U.S. Pat. No. 7,211,390; or those used in sequencing methods such as those described in U.S. Publication 2006/0024681, each of which is incorporated herein by reference.

FIG. 7 is an enlarged illustration of one of the sample areas of the microarray of FIG. 6. As shown in FIG. 6, the sample area 72 may contain a plurality of sections 76 that will be scanned by an imaging system in parallel scan lines that progressively move along the sample. In practice, a point may be scanned over a region of the sections corresponding to each of scan lines. Moreover, in many systems the microarray will be moved slowly, as indicated by arrow 78, while the imaging optic will remain essentially stationary. The parallel scan lines for imaging the sections 76 will then result from the progressive movement of the sample. It should also be noted that in practice, the entire width of the sample area or sections may be scanned, although alternative techniques may be used, including partial-width scanning of swaths followed by data stitching, as disclosed in U.S. Pat. No. 7,769,548, which is incorporated herein by reference.

FIG. 8 illustrates an exemplary section 76 that may itself include a plurality of domains 28, each populated by individual sites of biological material of interest. The layout of the sites within each domain will be hexagonal, as described above, but the orientation of the layouts of the sites within the domains will differ or alternate so as to enhance the readability and distinguishability of the sites, and reduce error in indexing or addressing the sites and therefor in the analysis of image data obtained. Each of the domains is separated from others by small spaces or edges 30 which may contain few or no sites.

An increasing number of applications have been developed for substrates with sites having biological molecules such as nucleic acids and polypeptides. Such microarrays typically include deoxyribonucleic acid (DNA) and ribonucleic acid (RNA) probes. These are specific for nucleotide sequences present in genes in humans and other organisms. In certain applications, for example, individual DNA and RNA probes can be attached at small locations in a geometric grid (or randomly) on a microarray support. A test sample, such as from a known person or organism, can be exposed to the grid, such that complimentary genes of fragments hybridize to probes at the individual sites in the array. The array can then be examined by scanning specific frequencies of light over the sites to identify which genes or fragments in the sample are present, by fluorescence of the sites at which genes or fragments hybridized.

In similar applications, biological microarrays may be used for genetic sequencing and similar applications. In general, genetic sequencing consists of determining the order of nucleotides or nucleic acid in a length of genetic material, such as a fragment of DNA or RNA. Relatively short sequences are typically analyzed, and the resulting sequence information may be used in various bioinformatics methods to logically fit fragments together so as to reliably determine the sequence of much more extensive lengths of genetic material from which the fragments were derived. Automated, computer-based examination of characteristic fragments have been developed, and have been used more recently in genome mapping, identification of genes and their function, and so forth. Microarrays are particularly useful for characterizing genomic content because a large number of variants are present and this requires many experiments to be performed in order for a statistically relevant data set to be acquired. The microarray is an ideal format for such investigations to be completed in a practical manner.

For these and other applications of substrates, improvements have recently been made in imaging systems for capturing data related to the individual molecules attached at sites of the microarrays. For example, improvements in imaging systems allow for faster, more accurate and higher resolution scanning and imaging, particularly through the use of line-scanning and confocal control of imaging optics. However, as the density of microarrays increases, and the size of the areas containing individually characterized sites also increases, scanning, both by point scanning and line scanning approaches becomes problematic. In particular, the maximum density of spherical shaped objects laid out upon a two-dimensional surface is achieved when those objects are configured in a hexagonal array. This format minimizes the amount of interstitial space. The total number of objects in a microarray is determined by the size of the active area and the density of the objects throughout that area. Maximizing the object density while maintaining a robust performance (e.g., detectability and accuracy of interpretation) is a goal for microarray designs because the larger number of experiments that can be accurately performed in a given area, the greater the information content of the array as more variants may be investigated simultaneously.

The maximum density of a microarray design is achieved when the diameter of each object and the pitch (center-to-center spacing) are minimized and equal to one another. The theoretical limit of this reduction is the physical dimensions of the system being studied (single molecule limit). A practical limitation, however, to the density of a realized array is influenced by three factors: (1) the method of detecting the signal from each unique object; (2) differentiating the signal from each object relative to the signal arising from neighboring objects; and (3) the ability to identify each object when a fraction of, or all neighboring objects are not detectable.

The capacity to identify each object in an array is derived from the ability to identify the location of each object as well as the characteristic form of the object's signal. The difficulty of the first task is compounded when a fraction of the objects are not detectable, such as when multiple objects do not generate detectable assay signals or are missing. Robust identification of each object in the array requires that additional information content be included in the design so that even extremely distorted signals will yield information about the unique location of each object and an empirical method to determine the form of the characteristic signal so that neighboring signals (crosstalk) may be taken into account when assigning a measured quantity to each particular object.

Figure 9:
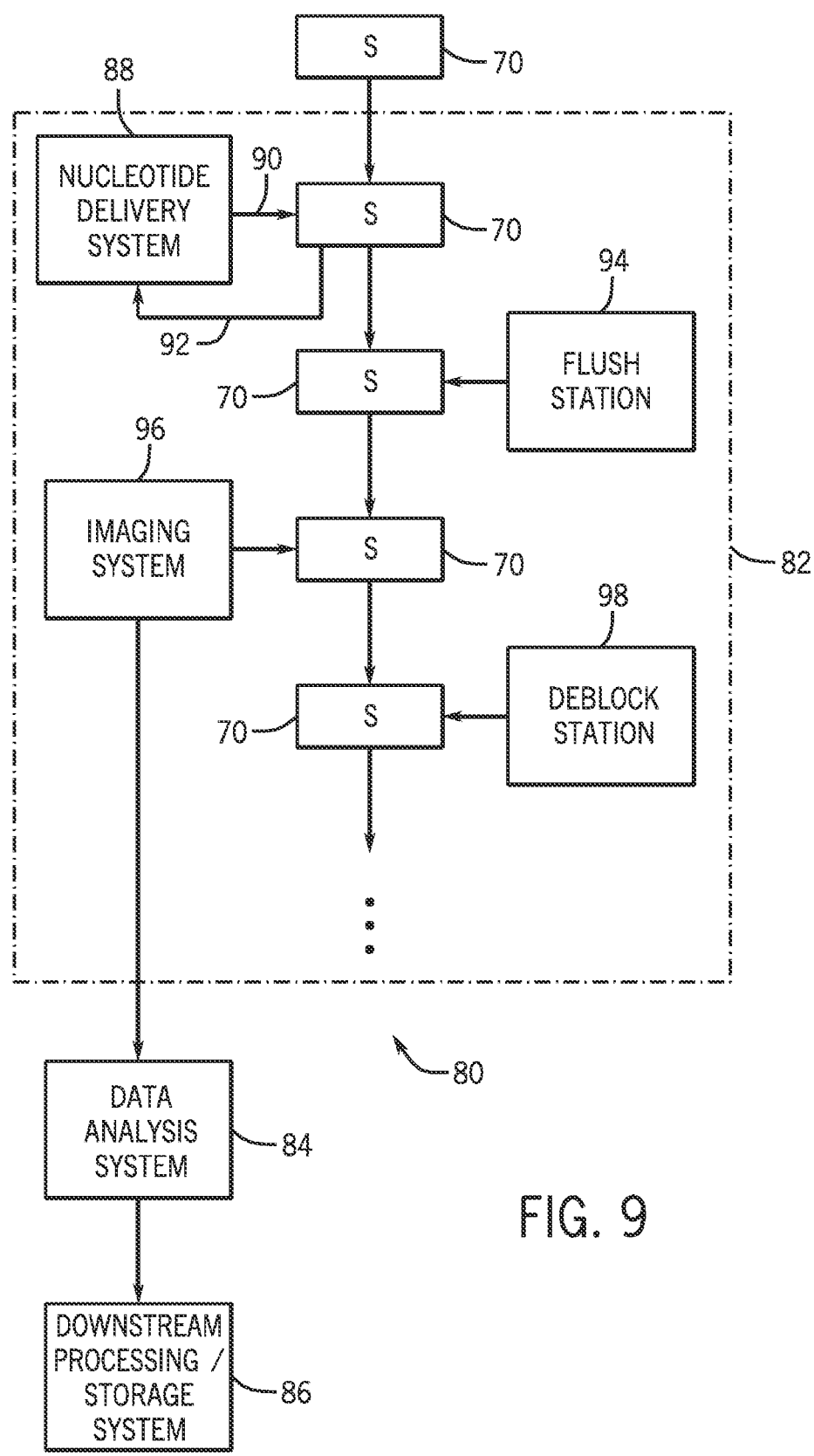
FIG. 9 is a diagrammatical overview of a substrate imaging and image processing system that might be utilized in connection with processing of a microarray of the type disclosed.

The foregoing site arrangements may be used in connection with a range of experiments, processes, evaluations and detection techniques, such as genotyping, genome sequencing, molecular characterization, and so forth. FIG. 9 illustrates an exemplary analysis system 80 for processing substrates of the type disclosed, imaging the microarrays, and analysis of data based upon the images. In the illustrated embodiment, the system is designed to introduce molecules, such as nucleotides, oligonucleotides, and other bioactive reagents into microarrays 70 that may be prepared in advance. The system may be designed for synthesizing biopolymers, such as DNA chains, or sequencing biopolymers. However, it should be borne in mind that the present technique is not limited in any way to sequencing operations, gene expression operations, diagnostic applications, diagnostic applications, or any one of these, but may be used in any of them for analyzing collected image data for multiple domains and sites of sample areas of a microarray as described below. Other substrates containing arrays of molecules or other detectable features can similarly be used in the techniques and arrays set forth herein.

In the illustrated embodiment, however, exemplary biopolymers might include, but are not limited to, nucleic acids, such as DNA, RNA or analogs of DNA or RNA. Other exemplary biopolymers might include proteins (also referred to as polypeptides), polysaccharides or analogs thereof. Although any of a variety of biopolymers may be used, for the sake of clarity, the systems and methods used for processing and imaging in the exemplary context illustrated in FIG. 9 will be described with regard to processing of nucleic acids. In general, the system illustrated in FIG. 9 will act upon microarrays 70 which may include arrays of reaction sites divided into domains. As used herein, the term "array" or "microarray" refers to a population of different reaction sites on one or more substrates such that different reaction sites can be differentiated from each other according to their relative location. Typically, a single species of biopolymer may be attached to each individual reaction site. However, multiple copies of particular species of biopolymer can be attached to a particular reaction site. The array taken as a whole will typically include a plurality of different biopolymers attached at a plurality of different sites. Reaction sites can be located at different addressable locations on the same substrate as described below. Alternatively, an array can include separate substrates, such as beads, each bearing a different reaction site. The sites may include fragments of DNA attached at specific locations in an array or may be wells in which a target product is to be synthesized. In certain applications, the system may be designed for continuously synthesizing or sequencing molecules, such as polymeric molecules based upon common nucleotides.

In the diagrammatical representation of FIG. 9, analysis system 80 may include a processing system 82 designed to process microarrays, typically substrates, and to generate image data representative of individual sites on the microarrays, as well as spaces between sites. A data analysis system 84 receives the image data and processes the image data in accordance stored routines, such as routines for signal filtering, registration, indexing, and so forth, to extract meaningful values from the imaging data. A downstream processing/storage system 86, then, may receive this information and store the information, along with imaging data, where desired. The downstream processing/storage system may further analyze the image data or the data derived from the image data, such as to diagnose medical conditions, compile sequencing lists, analyze gene expression, and so forth.

The processing system 82 may employ a bio-molecule reagent delivery system 88 for delivering various reagents to a microarray 70 as it progresses through the system. In general, system 82 may include a plurality of stations through which microarrays and microarray containers progress. This progression can be achieved in a number of ways including, for example, physical movement of the microarray to different stations, physical movement of different stations to a microarray, delivery of fluid from different stations to a microarray such as via valve actuation or some combination thereof. A system may be designed for cyclic operation in which reactions are promoted with single nucleotides or with oligonucleotides, followed by flushing, imagining and de-blocking in preparation for a subsequent cycle. In a practical system, the microarrays may be circulated through a closed loop path for sequencing, synthesis, ligation, or any other suitable process. Again, it should be noted that the process illustrated in FIG. 9 is by no means limiting, and the present invention may operate on image data acquired from any suitable system employed for any application.

In the illustrated embodiment, the nucleotide delivery system 88 provides a process stream 90 to the microarrays 70. An effluent stream 92 from the container may be recaptured and recirculated in the nucleotide delivery system. In the illustrated embodiment, then, the microarray container may be flushed at a flush station 94 to remove additional reagents and to clarify the microarray for imaging. The microarray is then moved to an imaging system 96 where image data may be generated that can be analyzed for determination of the sequence of a progressively building nucleotide chain, such as based upon a template. In a presently contemplated embodiment, for example, imaging system 96 may employ confocal line scanning to produce progressive pixilated image data that can be analyzed to locate individual sites in an array, including sites of different domains having differently oriented layouts, and to determine the type of nucleotide that was most recently attached or bound to each site. Other imaging techniques may also suitably be employed, such as techniques in which one or more points of radiation are scanned along the microarray.

Following imaging station 96, then, the microarrays may progress to de-blocking station 98 in which a blocking molecule or protecting group is cleaved from the last added nucleotide, along with a marking dye. If system 82 is used for sequencing, by way of example, image data from the imaging system 96 will be stored and forwarded to a data analysis system as indicated generally at reference numeral 84.

The analysis system will typically include a general purpose or application-specific programmed computer providing for user interface and automated or semi-automated analysis of the image data to determine which of the four common DNA nucleotides was last added at each of the sites in an array of each microarray, as described below. As will be appreciated by those skilled in the art, such analysis is typically performed based upon the color of unique tagging dyes for each of the four common DNA nucleotides. This image data may be further analyzed by the downstream processing/storage system 86, which may store data derived from the image data as described below, as well as the image data itself, where appropriate. Again, the sequencing application is intended to be one example only, and other operations, such as diagnostic applications, clinical applications, gene expression experiments, and so forth may be carried out that will generate similar imaging data operated on by the present invention. Some examples of array based methods that generate image data that can be made and used in accordance with the teachings herein include array-based genotyping or expression analyses, or decoding to determine the position of particular probes in random arrays.

Figure 10:
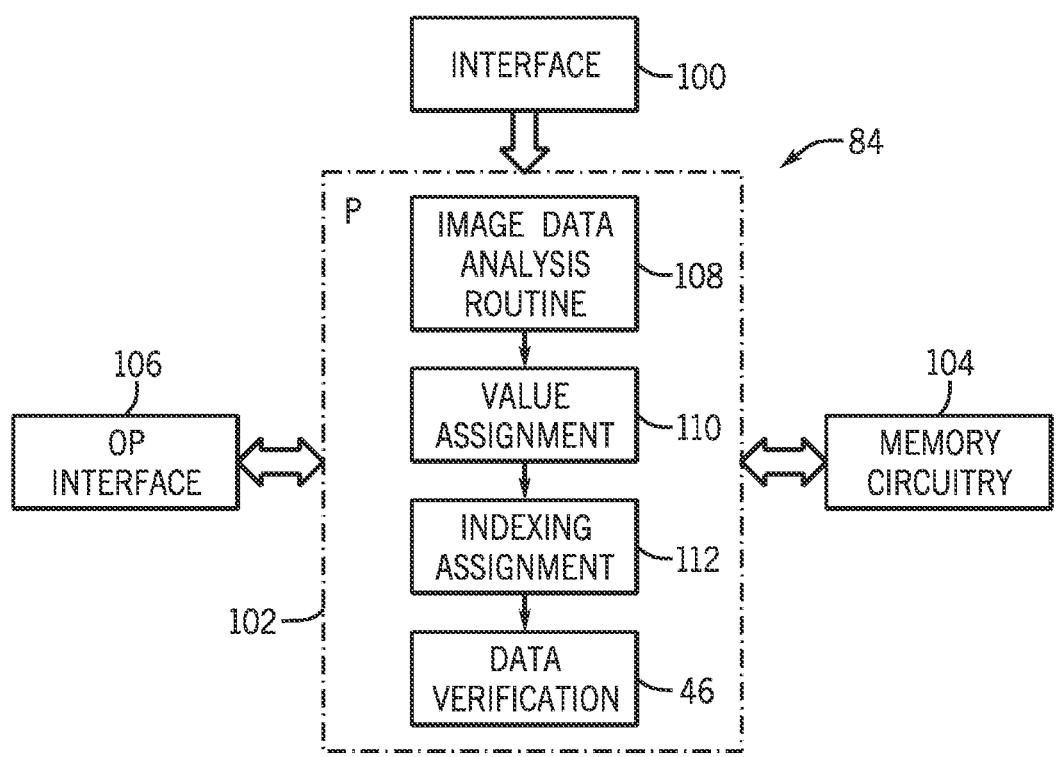
FIG. 10 is a diagrammatical overview of certain of the functional components that may be included in a data analysis system for use in a system of the type illustrated in FIG. 9.

FIG. 10 illustrates an exemplary data analysis system 84 and certain of its functional components insomuch as they relate to the present invention. As noted above, the system will typically be formed by one or more programmed computers, with programming being stored on one or more machine readable media with code executed to carry out processes described herein. In the illustrated embodiment, for example, the system includes an interface 100 designed to permit networking of the system to one or more imaging systems acquiring image data of substrates. The interface may receive and condition data, where appropriate. In general, however, the imaging system will output digital image data representative of individual picture elements or pixels that, together, form an image of the substrate. A processor, denoted generally by reference numeral 102 in FIG. 10, processes the received image data in accordance with a plurality of routines defined by processing code. The processing code may be stored in various types of memory circuitry, as represented generally by reference numeral 104 in FIG. 10.

In accordance with the presently contemplated embodiments of invention, the processing code executed on the image data includes an image data analysis routine 108 designed to analyze the image data to determine the locations of individual sites visible or encoded in the image data, as well as locations in which no site is visible (i.e., where there is no site, or where no meaningful radiation was detected from an existing site). As will be appreciated by those skilled in the art, in a typical substrate imaging setting, locations in the microarray will typically appear brighter than non-site locations due to the presence of fluorescing dyes attached to the imaged molecules. It will be understood that the sites need not appear brighter than their surrounding area, for example, when a target for the probe at the site is not present in a microarray being detected. The color at which individual sites appear may be a function of the dye employed as well as of the wavelength of the light used by the imaging system for imaging purposes. Sites to which targets are not bound or that are otherwise devoid of a particular label can be identified according to other characteristics, such as their expected location in the microarray.

It may be noted that as in the illustration of FIG. 10, an operator interface 106 is typically provided, which may consist of a conventional computer monitor, keyboard, mouse, and so forth to interact with the routines executed by the processor 102. The operator interface may be used to control, visualize or otherwise interact with the routines as imaging data is processed, analyzed and resulting values are indexed.

Once the image data analysis routine 108 has located individual sites in the image data, a value assignment may be carried out as indicated at reference numeral 110. In general, the value assignment carried out at step 110 will assign a digital value to each site based upon characteristics of the image data represented by pixels at the corresponding location. That is, for example, the value assignment routine 110 may be designed to recognize that a specific color or wavelength of light was detected at a specific location, as indicated by a group or cluster of pixels at the location. In a typical DNA imaging application, for example, the four common nucleotides will be represented by separate and distinguishable colors. Each color, then, may be assigned a value corresponding to that nucleotide. The value assignment carried out by routine 42, then, will assign the corresponding value to the entire site, alleviating the need to further process the image data itself, which will typically be much more voluminous (i.e., many pixels may correspond to each site) and of significantly larger numerical values (i.e., much larger number of bits to encode each pixel).

An indexing assignment routine 112, then, will associate each of the assigned values with a location in an image index or map. The map will correspond to the known or determined locations of individual sites within the microarray, with the sites being located in differently oriented layouts by domain, as described above. The present technique allows for indexing the assigned values by reference to one or more known features, such as an edge or another feature of interest (e.g., a notch, a particular pattern, a fiducial marker, etc.). Finally, a verification routine 46 may be performed, such as to verify alignment of the sites within a series of images, the indexing of the sites, and the quality of the data obtained.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An article of manufacture, comprising:
   (a) a substrate having a surface
   (b) a plurality of sites comprising one or more chemical moieties or biological molecules disposed at respective discrete locations on the surface and organized in at least one sample area, each sample area comprising at least two neighboring domains
   (c) a first domain of the at least two neighboring domains having a first layout comprising sites in a regular pattern and
   (d) a second domain of the at least two neighboring domains having a second layout comprising sites in the regular pattern, the regular pattern being oriented differently in the second layout relative to the first layout.

2. The article of claim 1, comprising at least two sample areas.

3. The article of claim 1, wherein the domains of a sample area are arranged in rows and columns.

4. The article of claim 1, wherein each domain comprises at least 1000 sites.

5. The article of claim 1, wherein no sites are disposed in the areas between neighboring domains.

6. The article of claim 1, wherein the regular pattern comprises a rectangular pattern.

7. The article of claim 1, wherein the regular pattern comprises a triangular or pentagonal pattern.

8. The article of claim 1, wherein the regular pattern comprises a hexagonal pattern.

9. The article of claim 1, wherein the regular pattern in a domain exhibits at least one angle interval of rotational symmetry, and the angles of neighboring domains differ from each other by an amount that is not equal to an angle interval.

10. The article of claim 1, wherein the second layout is angularly-displaced by about 45 degrees with respect to the first layout.

11. The article of claim 1, having four different layouts.

12. The article of claim 11, wherein the layouts are angularly-displaced by about 15, about 30, and about 45 degrees with respect to each another.

13. The article of claim 1, wherein the sites contain chemical groups.

14. The article of claim 1, wherein the minimum distance between any two sites is at most 2 microns.

15. The article of claim 1, wherein a plurality of sites are wells.

16. The article of claim 15, wherein the wells are at most 1.2 microns across.

17. The article of claim 1, wherein a plurality of sites support a material of interest.

18. The article of claim 17, wherein the material is a biological molecule.

19. The article of claim 17, wherein, within a single sample area, the sites support a plurality of different materials.

20. The article of claim 19, wherein each sample area supports greater than 1000 different materials.

21. The article of claim 1, wherein each individual site within the regular pattern comprises a plurality of molecules of a single type.

22. The article of claim 1, comprising a plurality of different biopolymers such that the plurality of sites of the regular pattern have different attached biopolymers relative to one another.

23. The article of claim 1, wherein each individual site within the pattern comprises at least one bead.

24. The article of claim 1, wherein each individual site has a diameter of 1.2 microns.

25. The article of claim 1, wherein the plurality of sites are separated by a uniform pitch.

* * * * *